United States Patent [19]

Suzuki et al.

[11] 4,377,615

[45] Mar. 22, 1983

[54] NONWOVEN FABRICS AND METHOD OF PRODUCING THE SAME

[75] Inventors: Migaku Suzuki; Takamitsu Igaue, both of Kawanoe, Japan

[73] Assignee: Uni-Charm Corporation, Ehime, Japan

[21] Appl. No.: 302,152

[22] Filed: Sep. 14, 1981

[30] Foreign Application Priority Data

Sep. 20, 1980 [JP] Japan .................. 55-131128

[51] Int. Cl.³ .................. A61F 13/16; B32B 5/26; B32B 5/28
[52] U.S. Cl. .................. 428/213; 128/290 W; 156/176; 156/305; 428/218; 428/286; 428/287; 428/288
[58] Field of Search .................. 128/290 W; 428/213, 428/218, 286, 287, 288; 156/176, 305

[56] References Cited

U.S. PATENT DOCUMENTS

| | | | |
|---|---|---|---|
| 1,961,914 | 6/1934 | Richter et al. | 428/218 |
| 3,923,931 | 12/1975 | Fechillas | 128/290 W |
| 3,978,257 | 8/1976 | Ring | 428/218 |
| 4,216,772 | 8/1980 | Tsuchiya et al. | 128/290 W |
| 4,307,721 | 12/1981 | Tsuchiya et al. | 128/290 W |
| 4,332,253 | 6/1982 | Schoots | 428/287 |

FOREIGN PATENT DOCUMENTS

| | | | |
|---|---|---|---|
| 491646 | 12/1975 | Australia | 428/218 |
| 2508987 | 9/1976 | Fed. Rep. of Germany | 428/218 |

*Primary Examiner*—James C. Cannon
*Attorney, Agent, or Firm*—Fred Philpitt

[57] ABSTRACT

A nonwoven fabrics comprising an upper layer having a substantially smooth surface and a lower layer having a density lower than that of the upper layer is provided; wherein the upper layer contains, as a principal element thereof, hydrophobic fibers, denier thereof being finer than in the lower layer, and containing a larger amount of adhesive bonding materials than in the lower layer; the lower layer contains, as a constituent fiber thereof, hydrophilic fibers and hydrophobic fibers, denier thereof being coarser than in the upper layer, and containing a smaller amount of adhesive bonding materials than in the upper layer.

14 Claims, 4 Drawing Figures

NONWOVEN FABRICS AND METHOD OF PRODUCING THE SAME

BACKGROUND OF THE INVENTION

The present invention relates to nonwoven fabrics having a multilayer structure and a method of producing the same. More particularly, the present invention relates to an improvement in a nonwoven fabric comprising a surface substantially smooth, an upper layer having high density and a lower layer having low density, and in a method of producing such fabric.

A nonwoven fabric of the type comprising a surface substantially smooth, an upper layer having high density and a lower layer having low density is used generally as an outer cover member of body exudates treatment articles, such as sanitary napkins, disposable diapers and the like. This type of nonwoven fabric, however, is not in a satisfactory degree in its capability preferably required as said outer cover member, that is, in smoothness, touch and strength of its surface; in bulkiness and cushion of entire structure, particularly in its lower layer, when in wetted state; and in surface permeability of body exudate when it is in a state of being in contact with the body exudate.

The present invention is not necessarily limited to a nonwoven fabric to be employed as an outer cover member of said body exudates treatment article and a method of producing such nonwoven fabric. It is to be understood, that the invention primarily aims at providing a nonwoven fabric which is preferable to dissolve the disadvantages seen in the prior art described above, and an improvement in a method of producing such nonwoven fabric.

A principal object of the present invention is to provide an arrangement to obtain a nonwoven fabric which is excellent in smoothness, touch and strength of its upper layer surface, wherein the arrangement comprises the step of distributing fibers with a relatively fine denier and a relatively large amount of adhesive bonding materials onto the upper layer of the nonwoven fabric, and a method of producing such nonwoven fabric.

Another object of the present invention is to provide an arrangement to obtain a nonwoven fabric which is excellent in bulkiness and cushion in its entire structure, particularly in its lower layer, and such excellency does not fall even in wetted state, wherein the arrangement comprises the step of distributing fibers with a relatively coarse denier, a relatively small amount of adhesive bonding materials, and a preferable amount of hydrophobic fibers onto the lower layer of the nonwoven fabric, and a method of producing such nonwoven fabric.

Still another object of the present invention is to provide an arrangement to obtain a nonwoven fabric which is superior in permeability and in preventing back flow of body exudates against the nonwoven fabric and which can maintain dryness in the surface thereof, wherein the arrangement comprises the steps of giving preferable density to both the upper layer and the lower layer of the nonwoven fabric with employment of adhesive bonding materials having preferable property and distributing a preferable amount of hydrophobic fibers and hydrophilic fibers to each layer, and a method of producing such nonwoven fabric.

Other objects of the present invention will become apparent from the following description.

The present invention provides an improvement in a nonwoven fabric and in a method of producing the same wherein: in a nonwoven fabric consisting of an upper layer having a substantially smooth surface and a lower layer having a density lower than that of the upper layer; the improvement which comprises a structure wherein said upper layer contains hydrophobic fibers of 80–100% by weight of its constitutional fibers, denier thereof being finer than in said lower layer, and containing a larger amount of adhesive bonding materials than in said lower layer; said lower layer contains hydrophilic fibers of 40–80% by weight of its constitutional fibers and hydrophobic fibers of 20–60% by weight of its constitutional fibers and these fibers are uniformly mixed, denier thereof being coaser than in said upper layer, and containing a smaller amount of adhesive bonding materials than in said upper layer.

The terms "upper layer" and "lower layer" used in the present invention do not indicate a state wherein thickness of a nonwoven fabric is equally divided into two but indicate a case wherein in a state of a plurality of fibrous webs formed through mixing of different fibers being overlapped to constitute a nonwoven fabric, such nonwoven fabric is divided into an upper layer having a relatively higher density and a lower layer having a relatively lower density. The term "density" means a case wherein the amount of fibers and adhesive bonding materials in each of the upper layer and the lower layer is averaged. The terms "containing amount of adhesive bonding materials" and "denier" mean a case wherein a containing amount of adhesive bonding materials and denier of the fibers in the upper layer and the lower layer are averaged.

DESCRIPTION OF THE PREFERRED EMBODIMENTS

Figure 1:
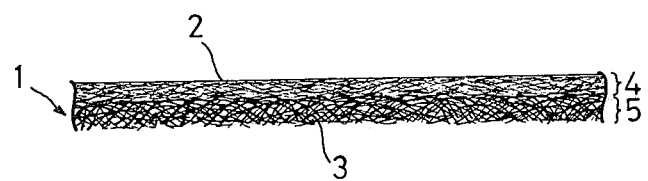
FIG. 1 is an enlarged schematic cross section of a nonwoven fabric according to the present invention.

Referring to FIG. 1, reference number 1 designates generally a nonwoven fabric according to the present invention. The nonwoven fabric 1 consists of an upper layer 4 having a substantially smooth surface 2 and of a lower layer 5 having a fluffing back surface 3. The upper layer 4 contains hydrophobic fibers of 80–100% by weight of its constitutional fibers, denier thereof being finer than in said lower layer 5, and containing a larger amount of adhesive bonding materials and having higher density than in said lower layer 5. The lower layer 5 contains hydrophilic fibers of 40–80% by weight of its constitutional fibers and hydrophobic fibers of 20–60% by weight of its constitutional fibers and these fibers are evenly mixed, denier thereof being coarser than in said upper 4, and containing a smaller amount of adhesive bonding materials and having lower density than in said upperlayer 4.

The fiber of the upper layer 4 is 1–4 denier, with a containing amount of adhesive bonding materials within 15–40% by weight thereof and with density of 0.01–1.17 g/cm$^3$. The fiber of the lower layer 5 is 3–9 denier, with a containing amount of adhesive bonding materials within 0.5–5% by weight thereof and with density of 0.003–0.06 g/cm$^3$. Weight of the nonwoven fabric 1 is 8–60 g/m$^2$, weight of the upper layer 4 is 5–35 g/m$^2$ and weight of the lower layer 5 is 3–25 g/m$^2$. Although the fiber length of the upper layer 4 and the lower layer 5 is not particularly limited, a fiber with length of 25–70 mm is used. As the fiber for the upper layer 4 and the lower layer 5, a fiber of the type used generally for a woven fabric, a nonwoven fabric and the like, for example, polyester, polypropylene, acrylic, rayon, acetate and the like, is used independently or in combination.

It is preferable that the fiber of the upper layer 4 consists of hydrophobic fibers of 100% by weight of its constitutional fibers, but such fiber may alternatively contain hydrophilic fibers less than 20% by weight. Where hydrophilic fibers more than 20% by weight are contained in the upper layer 4, adhesive bonding materials preferentially adhere to the hydrophilic fibers whereby strength of the upper layer 4 improves, but due to too high density brought about thereby, the layer becomes hard and the touch thereof becomes rough. Where hydrophilic fibers less than 40% by weight and hydrophobic fibers more than 60% by weight are contained in the lower layer 5, permeability in the lower layer 5 decreases and the adhesion strength becomes rather low whereby stability of the lower layer 5 is lost. Contrary, where hydrophilic fibers more than 80% by weight and hydrophobic fibers less than 20% by weight are contained in the lower layer 5, water absorption and retainability in the lower layer 5 become high, permeability becomes low, and adhesive strength among each fibers becomes too much whereby bulkiness and cushion of the lower layer 5 are lowered.

In order to attain the aforementioned objects of the present invention and to provide the upper layer 4 and the lower layer 5 with the aforementioned ability, it is necessary to see that not only the difference in containing of the hydrophobic fibers and the hydrophilic fibers, in the layers 4 and 5 but also the differences in denier, containing amount of adhesive bonding materials and density are within the aforementioned range. Property of adhesive bonding materials have an important relation, too. With a view to giving good feeling to the entire of the nonwoven fabric 1, improving its strength in wetted state, bettering its permeability and giving stability so as to be durable for a long time operation in the present method to be described later, an adhesive bonding material of the type comprising, as a main component, acrylic esters copolymer, containing suitable surface active agent, and further regulating a particle diameter of said copolymer emulsion, is used. More specifically, acrylic esters copolymer consists of monomer, such as ethyl acrylate, methyl acrylate and/or butyl acrylate, wherein ethyl acrylate stands as a main component and occupies preferably 60–95% by weight, more preferably 70–90% by weight. The surface active agent referred to above consists primarily of nonionic surface active agent and containing a small amount of anionic surface active agent coexisting with nonionic surface active agent, so as to obtain stability of a binder emulsion in the method according to the present invention to be described later. Preferably, nonionic surface active agent and anionic surface active agent are in the ratio of 9:1. Preferably, nonionic surface active agent is alkylether or alkylallylether which are ethylene oxide adduct with low HLB. This HLB is preferably 10–17, more preferably, less than 5. Ethylene oxide addition molar number is preferably more than 10.

Figure 2:
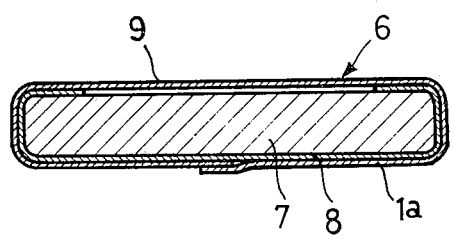
FIG. 2 is a cross section of a sanitary napkin, cut in its thickness direction in which a nonwoven fabric according to the present invention is used as an outer cover member.

The nonwoven fabric according to the present invention may preferably be used as an outer cover member of body exudates treatment articles, such as sanitary napkins, disposable diapers and the like. FIG. 2 exemplarily shows that the nonwoven fabric according to the present invention is used as an outer cover member for a sanitary napkin 6, wherein the napkin 6 consists of an absorptive core 7, a water-impervious sheet 8 disposed on the lower surface and on both sides of the absorptive core 7, and an outer cover member 1a according to the present invention. Where a surface 9 of the cover member 1a is not smooth and is rough to the touch, it results in giving the user discomfort; whilst where strength of the cover member 1a in wetted state is low, the cover member is liable to break during use and the absorptive core 7 may partially be exposed, whereby functions of the cover member cannot be fulfiled. Further, where bulkiness and cushion of the lower layer of the cover member 1a are low, such property of whole of the cover member drops and therefore it is not possible to give the user soft comfortableness. Where such drop in property of the cover member in wetted state is great, no sufficient space wherein fibers are to sparsely exist will be provided between the cover member 1a and the absorptive core 7, whereby spot absorption of body exudates in the surface 9 of the napkin 6 cannot be attained. Where an adhesive bonding material having preferable property is not used for the cover member 1a; where no preferable density is given to the upper layer and the lower layer of the cover member 1a; and where no preferable amount of hydrophilic fibers and hydrophobic fibers are distributed, permeability of body exudates in the surface 9 drops whilst body exudates are liable to ooze out. For this reason, proper dryness in the surface 9 is not retained, thus giving the user uncomfortable wetted touch. Since the cover member 1a consists of the nonwoven fabric 1 according to the present invention, drawbacks as described above are not involved and therefore it can be said that the cover member 1a is suitable for the constituent element of body exudates treatment articles in the field referred to above.

Figure 3:
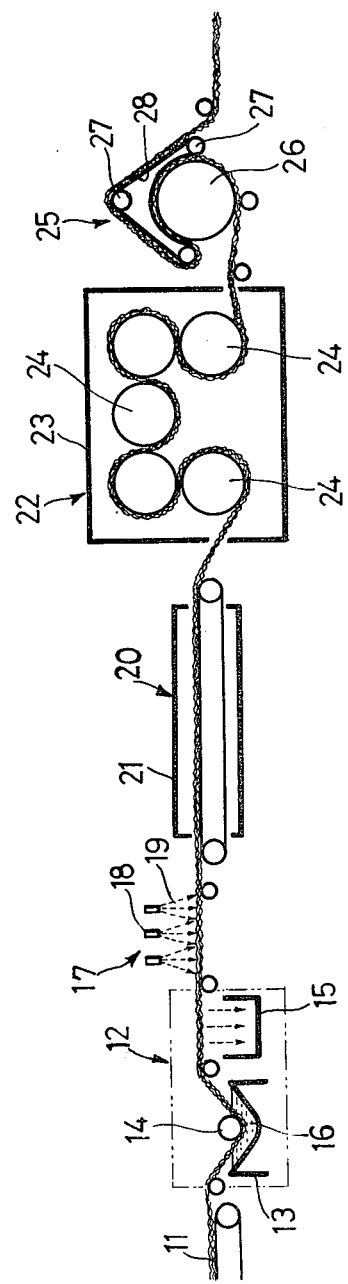
FIG. 3 is a schematic side elevation of an exemplary apparatus to carry out a method of producing nonwoven fabrics according to the present invention.

FIG. 3 exemplarily shows an apparatus to carry out the method of producing nonwoven fabrics according to the present invention. In operation, previously explained material fibers are prepared and formed into webs and are piled up by means of a plurality of cards (not shown). Number of layer of such piled up web 11 is more than two, preferably more than three. The upper layer of the web 11 corresponds to the upper layer 4 of the forementioned nonwoven fabric 1, in FIG. 3. The web 11 is guided to a saturator 12. The saturator 12 is provided with an apron 13, a roll 14 and a suction 15, the web 11 being dipped in a binder emulsion 16 having solid content of 0.5–5%. The amount of binder emulsion 16 is adjusted by the suction 15 so that the pickup amount thereof with respect to the web 11 may be within the range of 200–400% relative to weight of the fibers of the web. The web 11 is guided further to a spraying apparatus 17. The apparatus 17 is provided with a plurality of nozzles 18. Binder emulsion 19 is sprayed from the nozzles 18 onto the surface of the web 11, the binder emulsion 19 having solid content of 5-15%, in such a manner that a pickup amount with respect to the web is within the range of 50-200% relative to the fibers of the upper layer of the web. The web 11 treated with the binder emulsion in this manner will then be guided to a first dryer 20. he first dryer 20 comprises a heat tunnel 21, a circulating fan and an exhaust fan (both fans not shown in the drawings), the web 11 is preliminarily treated by the hot air. The web 11 is further guided to a second dryer 22. The second dryer 22 comprises a box 23 in which there is disposed a plurality of suction drums 24 having porous surfaces with mesh of 10. The web 11 is treated by each of the drums. The web 11 is further guided to a third layer 25. The third layer 25 comprises a cylinder 26 having a smooth surface and a canvas felt 28 forcibly pressed against the surface of the cylinder 26 via a plurality of rolls 27, whereby the web 11 is forcibly pressed against the surface of the cylinder 26 by means of the felt 28 and is cured. The resultant web 11 is of substantially smooth surface.

Figure 4:
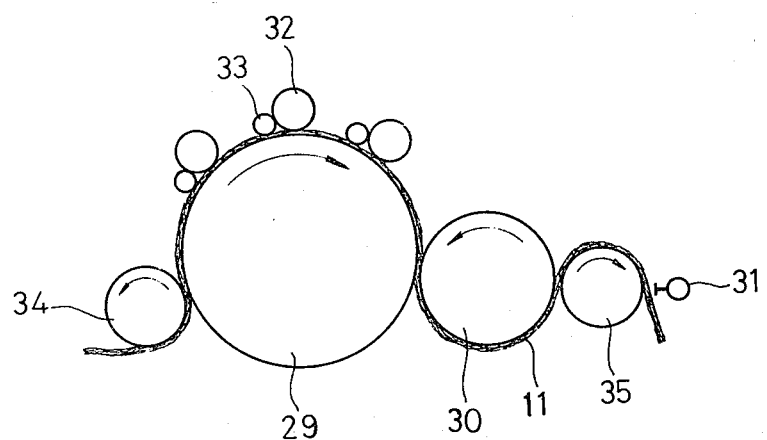
FIG. 4 is a schematic side elevation of a card to form one preferable material web for a nonwoven fabric according to the present invention.

FIG. 4 shows a preferable card to form a fibrous web 11 which is preferable as a raw material for the above-mentioned nonwoven fabric to be used in the present invention. This card comprises an arrangement wherein in an ordinary card mechanism having a cylinder 29, a doffer 30, a comber 31, a worker 32, a stripper 33 and a taker-in roller 34; a condensing roll 35 having a substantially same circumferential surface structure as that of the doffer 30 is disposed between the doffer 30 and the comber 31. The condensing roll 35 is designed so that its circumferential surface speed may be substantially lower than that of the doffer 30. With the use of such card as described, it is possible to contract the fibrous web 11 in its direction of flow by a cooperative action between the doffer 30 and the condensing roll 35, whereby the fiber is condensed. As such card, for example, the same one as what is manufactured by Helgeth Company, Dülmen, West Germany, is employed.

According to such card, the web 11 having randomized fibers is formed, being extremely rich in bulkiness and rather homgenized in directions.

EXAMPLE I, II, III, IV

Treatment raw material used in the EXAMPLE I is of the type wherein a web consisting of a mixture of polyester fibers (referred to as PET hereinafter) and polypropylene fibers (referred to as PP hereinafter) is arranged in the upper layer and web consisting of a mixture of PET, rayon fibers (referred to as RAY hereinafter) and PP is arranged in the lower layer, and these webs are piled.

Treatment raw material used in the EXAMPLE II is of the type wherein a web consisting of a mixture of PET and PP is arranged in the uppermost layer, a web consisting of a mixture of PET and PP is arranged in the upper layer and a web consisting of a mixture of RAY and PP is arranged in the lower layer; and these webs are piled.

Treatment raw material used in the EXAMPLE III is of the type wherein a web consisting of a mixture of PET and PP is arranged in each of the uppermost layer and the upper layer and a web consisting of a mixture of RAY and PP is arranged in the lower layer; and these webs are piled.

Treatment raw material used in the EXAMPLE IV is of the type wherein a web consisting of a mixture of PET and PP is arranged in the upper layer, a web consisting of a mixture of PET, RAY and PP is arranged in the lower layer; and these webs are piled.

In every examples referred to above, the web was transferred into the apparatus shown in FIG. 3 at a rate of 30 m/min; the web was then dipped into the binder emulsion having solid content of 3% in the saturator and adjusted by the suction so that the pickup amount may nearly be 300% relative to the fibers of the web; and the binder emulsion having solid content of 10% was sprayed onto the surface of the upper layer of the web in the spraying apparatus so that the pickup amount may nearly be 100% relative to the fibers of the upper layer. Thereafter, the web was subjected to preliminary treating in the first dryer maintained at a temperature of 100° C., further subjected to treating in the second dryer maintained at a temperature of 130° C., and finally subjected to curing in the third dryer maintained at a temperature of 145° C. whereby the nonwoven fabric was obtained. As the said binder, copolymer emulsion which was copolymerized with ethyl acrylate and methylmethacrylate at the ratio of 8:2 and which contains surface active agent and anionic surface active agent at the ratio of 9:1 was used. The said emulsion was of the particle diameter of 334 m$\mu$ and of pH 7.

Table 1 shows the composition and strength of nonwoven fabric in Examples I, II, III and IV. Table 2 shows the composition and strength of nonwoven fabric in Comparative Examples I, II and III. Table 3 shows bulkiness, permeability rate and the back flow rate in Examples I, II, III and IV as well as in Comparative Examples I, II and III.

TABLE 1

| example | | Fiber | | | | | Binder quantity | | Density | | Strength (g/1p - 25mm) | | | |
|---|---|---|---|---|---|---|---|---|---|---|---|---|---|---|
| | | | | | | | | | | | Dry | | Wet | |
| | | Weight (%) | Denier | Length (mm) | Average denier | Weight (g/m$^2$) | Wt % | Ratio | Value (g/cm$^3$) | Ratio | MD | CD | MD | CD |
| I | Upper layer | PET 54.1 | 1.5 | 51 | | | | | | | | | | |
| | | PP 13.5 | 4 | 51 | 2.75 | 9.25 | 32.4 | 1 | 0.19 | 1 | | | | |
| | | PET 42.9 | 2 | 51 | | | | | | | 1782 | 140 | 720 | 63 |
| | Lower layer | RAY 28.3 | 8 | 51 | | | | | | | | | | |
| | | PP 26.9 | 3 | 51 | 4.33 | 15.75 | 1.6 | 0.05 | 0.02 | 0.01 | | | | |
| II | Uppermost layer | PET 72 | 1.5 | 51 | 2.75 | 15 | 20 | 1 | 0.42 | 1 | | | | |
| | | PP 8 | 4 | 51 | | | | | | | | | | |
| | upper layer | PET 43.6 | 2 | 51 | 3 | 7 | 12.8 | 0.51 | 0.1 | 0.23 | 2012 | 162 | 813 | 74 |
| | | PP 43.6 | 4 | 51 | | | | | | | | | | |
| | Lower layer | RAY 57.7 | 8 | 51 | 5.5 | 8 | 3.7 | 0.57 | 0.02 | 0.05 | | | | |
| | | PP 38.6 | 3 | 51 | | | | | | | | | | |
| III | Uppermost layer | PET 65.5 | 1.5 | 51 | 1.25 | 7.8 | 29.6 | 1 | 0.08 | 1 | | | | |
| | | PP 4.9 | 2 | 51 | | | | | | | | | | |
| | Upper layer | PET 67.8 | 2 | 51 | 3 | 7.5 | 27.2 | 0.88 | 0.04 | 0.5 | 1921 | 154 | 793 | 70 |
| | | PP 5 | 4 | 51 | | | | | | | | | | |

TABLE 1-continued

| example | | Fiber Weight (%) | Denier | Length (mm) | Average denier | Weight (g/m²) | Binder quantity Wt % | Ratio | Density Value (g/cm³) | Ratio | Strength (g/1p - 25mm) Dry MD | CD | Wet MD | CD |
| --- | --- | --- | --- | --- | --- | --- | --- | --- | --- | --- | --- | --- | --- | --- |
| | Lower layer | RAY 65.8 | 6 | 51 | 4.5 | 9.7 | 2.6 | 0.09 | 0.01 | 0.13 | | | | |
| | | PP 3.16 | 3 | 51 | | | | | | | | | | |
| IV | Upper layer | PET 63.2 | 1.5 | 51 | 2.25 | 10.1 | 28.4 | 1 | 0.16 | 1 | | | | |
| | | PP 8.4 | 3 | 51 | | | | | | | 12 | 1020 | 615 | 417 |
| | Lower layer | PET 26.4 | 2 | 51 | | | | | | | | | | |
| | | RAY 42 | 5 | 51 | 3.3 | 14.1 | 5.2 | 0.27 | 0.02 | 0.13 | | | | |
| | | PP 26.4 | 3 | 51 | | | | | | | | | | |

TABLE 2

| Comparative example | | Fiber Weight (%) | Denier | Length (mm) | Average denier | Weight (g/m²) | Binder quantity Weight (%) | Ratio | Density Value (g/cm³) | Ratio | Strength (g/1p - 25mm) Dry MD | CD | Wet MD | CD |
| --- | --- | --- | --- | --- | --- | --- | --- | --- | --- | --- | --- | --- | --- | --- |
| I | Upper layer | PET 20 | 4 | 42 | | | | | | | | | | |
| | | RAY 48 | 4 | 42 | 4 | 15 | 32 | 1 | 0.42 | 1 | | | | |
| | Lower layer | PET 32 | 6 | 51 | | | | | | | 1341 | 121 | 381 | 69 |
| | | RAY 31 | 8 | 51 | 6.7 | 15 | 20 | 0.62 | 0.17 | 0.4 | | | | |
| | | PP 17 | 6 | 51 | | | | | | | | | | |
| II | Single layer | RAY 75 | 5 | 51 | 5 | 25 | 25 | — | 0.81 | — | 1627 | 121 | 811 | 52 |
| III | Upper layer | PET 65 | 3 | 51 | 3 | 18 | 35 | 1 | 0.16 | 1 | | | | |
| | Lower layer | RAY 90 | 3 | 51 | 3 | 15 | 10 | 0.24 | 0.32 | 2 | 1421 | 112 | 512 | 57 |

TABLE 3

| | Bulk (mm/per sheet) | Permeability (%) | Back flow ratio (%) |
| --- | --- | --- | --- |
| Example I | 1.02 | 95 | 21 |
| Example II | 0.99 | 92 | 27 |
| Example III | 0.89 | 91 | 19 |
| Example IV | 1.12 | 93 | 19 |
| Comparative Example I | 0.67 | 83 | 32 |
| Comparative Example II | 0.41 | 87 | 14 |
| Comparative Example III | 0.52 | 52 | 8 |

(Note 1)
PET, RAY and PP in Comparative Examples I, II, III indicate the same fibers as those in Examples I, II, III and IV. Where more than two kinds of fibers are shown in one layer, a web consisting of a mixture of such fibers is indicated whilst where sole fiber is shown in one layer, a web consisting of such sole fiber is indicated.

(Note 2)
As regards the bulk, calculation was made under an arrangement wherein test samples cut into ten sheets so that each be of the size of 200mm × 200mm are piled and a plastic planar sheet with the size of 200mm × 200mm weighting 200g is disposed thereon and an entire thickness thereof is measured and finally a thickness per one sheet is calculated.

(Note 3)
As regards the permeability ratio, a test sample was supported at an angle of 45° and water was dropped from above sample at a speed of 5 ml per min., whereupon permeability was measured.

(Note 4)
As regards the back flow ratio, a test sample was disposed on a crushed pulp sandwiched between the tissue papers of the size 100mm × 100mm, water having weight of four times or more heavier than own weight of the text sample and the pulp was dropped, after one minute, pressure of 35g/cm² was given on the test sample and the pulp, whereupon the back flow ratio with the respect to the surface of the test sample was measured.

What is claimed is:

1. In a nonwoven fabric comprising an upper layer having a substantially smooth surface and a lower layer having a density lower than in said upper layer, the improvement which comprises a structure wherein said upper layer contains 80 to 100 percent hydrophobic fibers by weight of its constitutional fibers, denier thereof being finer than in said lower layer, and containing a larger amount of adhesive bonding materials than in said lower level; said lower layer contains 40 to 80 percent hydrophilic fibers by weight and 20 to 60 percent hydrophobic fibers by weight of its constitutional fibers and these fibers are uniformly mixed, denier thereof being coarser than in said upper layer, and containing a smaller amount of adhesive bonding materials than in said upper layer.

2. A nonwoven fabric as claimed in claim 1, wherein said upper layer contains less than 20 percent hydrophilic fibers by weight of its constitutional fibers.

3. A nonwoven fabric as claimed in claim 1, wherein the fibers of said upper layer is 1 to 4 denier and the fibers of said lower layer is 3 to 9 denier.

4. A nonwoven fabric as claimed in claim 1, wherein containing amount of adhesive bonding materials of said upper layer is 15 to 40 percent by weight of said upper layer and containing amount of adhesive bonding materials of said lower layer is 0.5 to 5 percent by weight and said lower layer.

5. A nonwoven fabric as claimed in claim 1, wherein a density of said upper layer is 0.01 to 1.17 g/cm³ and a density of said lower layer is 0.003 to 0.06 g/cm³.

6. A nonwoven fabric as claimed in claim 1, wherein said adhesive bonding materials consist primarily of copolymer of acrylic esters.

7. A nonwoven fabric as claimed in claim 6, wherein copolymer of acrylic esters consists of monomers of ethyl acrylate as main component and methyl acrylate and/or buthyl acrylate as additional component.

8. In a method of producing a nonwoven fabric comprising an upper layer having a substantially smooth surface and a lower layer having a density lower than in said upper layer, the improvement therein which comprises the steps of forming a fibrous web to be said upper layer, with 80 to 100 percent hydrophobic fibers by weight having denier finer than that of a fibrous web to be said lower layer; forming a fibrous web to be said lower layer, with a mixed fiber consisting of 40 to 80 percent hydrophilic fibers by weight and of 20 to 60 percent hydrophobic fibers by weight both having denier coarser than that of said web to be said upper layer and overlapping said webs; treating said overlapped web with a binder emulsion; treating the surface of the web of said upper layer with a binder emulsion so that said web may be provided with a larger amount of a binder than said web of said lower layer; and curing said overlapped web by forcibly pressing the web surface of said upper layer against a planar dry surface of a dryer so as to give said surface a substantially smooth finish.

9. A method of producing a nonwoven fabric as claimed in claim 8, wherein said web of said upper layer contains less than 20 percent hydrophilic fibers by weight of its constitutional fibers.

10. A method of producing a nonwoven fabric as claimed in claim 8, wherein the fibers of said web of said upper layer is 1 to 4 denier and the fibers of said web of said lower layer is 3 to 9 denier.

11. A method of producing a nonwoven fabric as claimed in claim 8, which comprises the steps of pickuping 200 to 400 percent binder emulsion by weight of 0.5 to 5 percent solution on said overlapped web; pickuping 50 to 200 percent binder by weight of 5 to 15 percent solution on said upper layer web; curing said overlapped web so that a containing amount of a binder with respect to said upper layer in a finished nonwoven fabric may be 15 to 40 percent by weight of said upper layer and so that a containing amount of a binder with respect to said lower layer in a finished nonwoven fabric may be 0.5 to 5 percent by weight of said lower layer.

12. A method of producing a nonwoven fabric as claimed in claim 8 or in claim 11, wherein said binder contains, as a main component, copolymer of acrylic esters.

13. A method of producing a nonwoven fabric as claimed in claim 12, wherein copolymer of acrylic esters consists of monomers of etyl acrylate as main component and methyl acrylate and/or butyl acrylate as additional component.

14. A method of producing a nonwoven fabric as claimed in claim 8 or in claim 11, wherein a density of said upper layer in a finished nonwoven fabric is arranged to be 0.01 to 1.17 g/cm$^3$ and a density of said lower layer in a finished nonwoven fabric is arranged to be 0.003 to 0.06 g/cm$^3$.

* * * * *